United States Patent [19]

Dwyer et al.

[11] 4,035,430
[45] July 12, 1977

[54] CONVERSION OF METHANOL TO GASOLINE PRODUCT

[75] Inventors: Francis G. Dwyer, West Chester, Pa.; Francis V. Hanson, Pitman, N.J.; Albert B. Schwartz, Philadelphia, Pa.

[73] Assignee: Mobil Oil Corporation, New York, N.Y.

[21] Appl. No.: 708,955

[22] Filed: July 26, 1976

[51] Int. Cl.$^2$ .......................................... C07C 1/20
[52] U.S. Cl. ...................... 260/668 R; 260/614 R; 260/668 D
[58] Field of Search ........ 260/614 R, 668 R, 668 D

[56] References Cited

U.S. PATENT DOCUMENTS

| | | | |
|---|---|---|---|
| 1,949,344 | 2/1934 | Woodhouse | 260/614 R |
| 3,928,483 | 12/1975 | Chang et al. | 260/614 R |

Primary Examiner—Veronica O'Keefe
Attorney, Agent, or Firm—Charles A. Huggett; Carl D. Farnsworth

[57] ABSTRACT

The conversion of methanol to gasoline boiling products in a plurality of sequentially arranged catalyst beds comprising a dehydration catalyst followed by a special class of crystalline zeolite conversion catalyst is described wherein the dehydration catalyst life is prolonged and durene formed in the process is recycled to the zeolite catalyst conversion step.

11 Claims, 4 Drawing Figures

Total Aromatics Yield
Durene Doping Experiments

C_5^+ Yield
Durene Doping Experiments

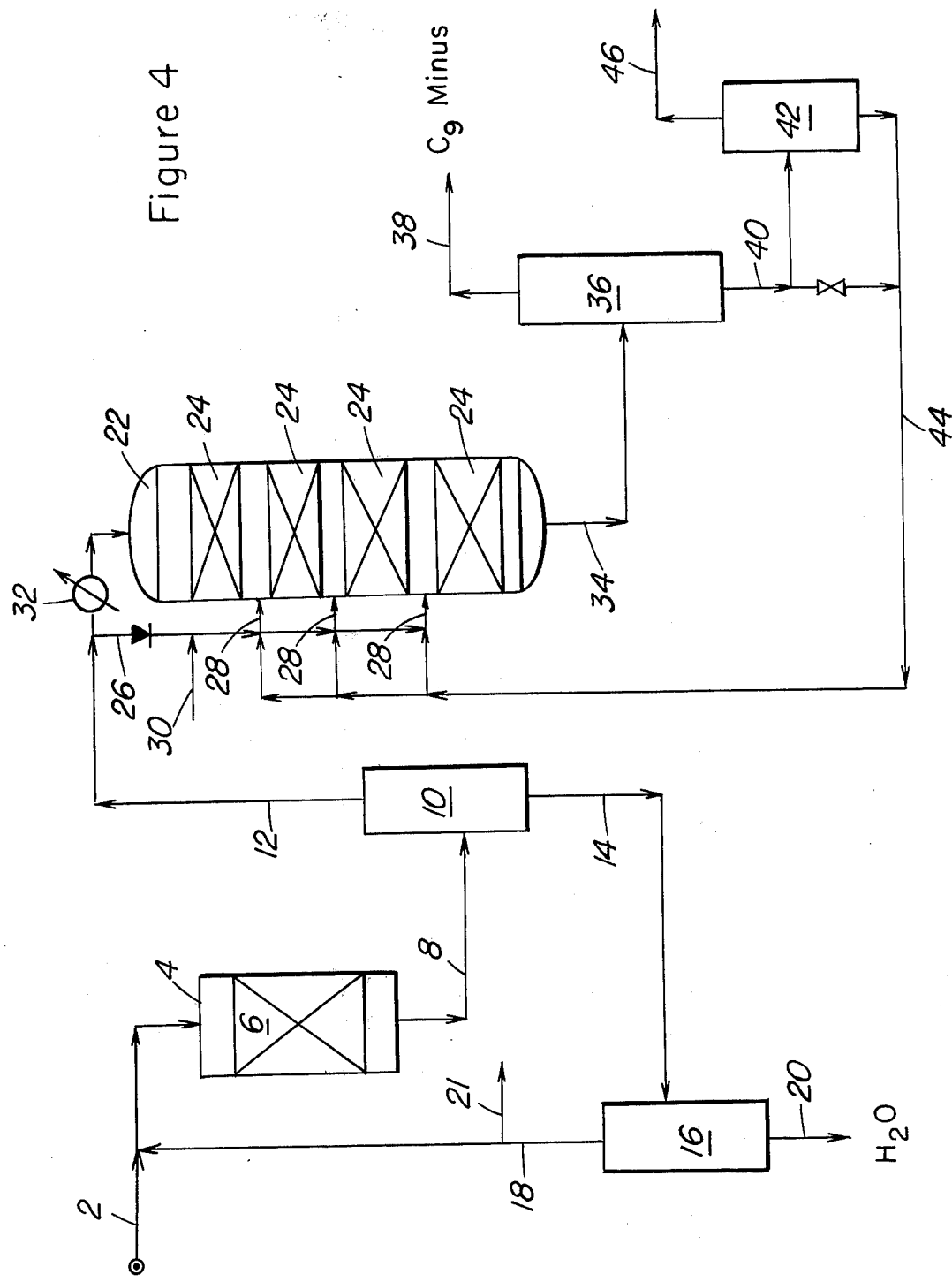

CONVERSION OF METHANOL TO GASOLINE PRODUCT

BACKGROUND OF THE INVENTION

The exothermic conversion of the lower alcohols such as methanol to its corresponding ether has been known to take place in the presence of certain catalysts such as gamma alumina.

Copending application Ser. No. 387,223 filed Aug. 9, 1973, discloses the conversion of alcohols to a reaction product containing water and highly aromatic, gasoline boiling range hydrocarbons by contact with a crystalline zeolite having a silica to alumina ratio of at least about 12 and a constraint index of about 1 to 12.

Other copending applications of interest include Ser. No. 382,222 filed Aug. 9, 1973; Ser. No. 358,192 (abandoned) filed May 7, 1973 and Ser. No. 130,442 (abandoned) filed Apr. 11, 1971. U.S. Pat. Nos. 3,702,886 issued Nov. 14, 1972 and 3,709,979 issued Jan. 9, 1973 are also of interest.

SUMMARY OF THE INVENTION

This invention relates to the method and system for converting methanol to gasoline boiling components. More particularly, the present invention relates to a sequential restructuring of methanol through a plurality of selective conversion catalysts contact zones temperature restrained within particularly desired limits in response to catalyst activity, selectivity and desired product yield. The invention relates to particularly accomplishing the sequential restructuring of vaporized methanol to an ether rich product such as dimethyl ether and conversion of the ether rich product to aromatics and isoparaffins boiling in the gasoline boiling range. In another aspect, the present invention relates to the method and combination of processing steps for catalytically restricting the conversion of methanol to durene as well as the exothermic temperature rise encountered in the restructuring operation to form a product rich in aromatic components such as BTX during contact with catalyst compositions suitable for effecting such conversion.

In the operation contemplated by the present invention, the large amount of heat released during the conversion of methanol to gasoline boiling components is controlled in a sequentially arranged catalyst environment employing one or more fluid or fixed catalyst bed conversion zones. The methanol feed either pure methanol or containing up to about 20% water is vaporized and converted initially to a mixture of dimethyl ether, methanol and water by contact with a mass of catalyst suitable for the purpose such as gamma alumina wherein the reaction heat generated amounts to within the range of about 15% to 20% of the total heat release for the complete conversion of the methanol charge to gasoline boiling components. This initial reaction heat so generated is released essentially under self-limiting conditions since the reaction step is equilibrium controlled. The initial exothermic conversion of the methanol feed to its ether product with the alumina catalyst heats the reactant to a temperature sufficiently high to initiate a subsequent conversion thereof to gasoline boiling range aromatics upon contact with a ZSM-5 class of crystalline zeolite in the absence of any interstage cooling to remove formed water. In the combination of operating restraints herein identified it has been found desirable to separate water and unconverted methanol from the ether product before contacting the ether rich product with the zeolite catalyst. In addition a light hydrocarbon gas comprising $C_5$ and lower boiling hydrocarbons may be used as a heat sink and carrier gas to distribute generated exothermic heat during the crystalline zeolite contact step. Water may also be used for emergency purposes but the use of significant amounts of water is desirably avoided for reasons herein expressed. In the combination operation above described, the temperature variation or increment in the ether forming step and the crystalline zeolite catalyst conversion step will be maintained within carefully controlled limits for the purpose of enhancing the combination to which the present invention is particularly directed.

The conversion of methanol to gasoline boiling components is a highly exothermic reaction releasing approximately 750 BTU of heat per pound of methanol. This amount of heat release will result in an adiabatic temperature increase of about 1200° F. for pure methanol feed. In an adiabatic catalyst bed reactor, this large temperature increase will result in high catalyst aging rates, and possibly cause thermal damage to the catalyst. Furthermore, such high temperatures could cause an undesirable product distribution to be obtained. Therefore, it is critical in the conversion of methanol to useful products to provide sufficient water removal and heat dissipating facilities so that temperatures encountered in any portion of the catalyst sequence are restricted within predetermined limit.

It is clear from the above brief discussion that a combination of at least two separate reaction temperature control mechanisms are relied upon and used in the combination of this invention. These temperature control mechanisms include a self-limiting conversion catalyst relied upon to promote the conversion of methanol to particularly dimethylether under carefully selected elevated temperature conditions to particularly eliminate or reduce the deactivation of the alumina catalyst caused by water in the feed. The temperature of the conversion of ether products thereof with a ZSM-5 type crystalline zeolite to components boiling in the gasoline boiling range may be controlled by the addition of a heat dissipating fluid, such as recycle, to the stream. This recycle may include durene. The other temperature control mechanism particularly employed is direct to using a heat dissipating material such as methanol, a dimethyl ether product thereof or a product of the process that may contain $C_{10}$ aromatics, such as, durene is passed in cooling contact with product material between beds of the crystalline zeolite conversion catalyst. Thus, the present invention contemplates the use of light hydrocarbon gases, $C_5$ and lower boiling material, in combination with methanol and or ether product effluent and particularly durene product material during contacting the ZSM-5 zeolite catalyst. By using a proper dilution ratio and catalyst bed arrangement, the exothermic temperature rise in the ZSM-5 catalyst reaction zone is readily controlled within desired practical limits restricted to a $\Delta T$ temperature rise per catalyst bed of about 50° F. The light hydrocarbon gases thus employed are easily separated from the higher boiling gasoline components and can be recycled to the reactor inlet as diluent as provided above. On the other hand a cool dimethylether charge alone or separated durene used alone or in combination therewith may be used with the light hydrocarbon cooling diluent.

The catalyst systems contemplated in the combination process of the present invention are selected from catalyst compositions particularly promoting the sequence of conversion steps herein defined. Thus it is proposed to use in the initial methanol conversion step, a selective catalyst composition which will particularly restrict the conversion of methanol to an ether component and thus restrict its exothermic temperature rise. The catalyst thus will release only a portion of the total exothermic heat resulting from the conversion of methanol to gasoline boiling components. A catalyst suitable for this purpose in the ether forming step is gamma alumina. The crystalline zeolite conversion catalyst relied upon to convert the dimethyl ether product formed from the methanol charge and any unconverted methanol in the ether containing effluent is preferably a special class of crystalline zeolite represented by a ZSM-5 crystalline zeolite material. However, other crystalline zeolites providing activity-selectivity characteristics similar to the ZSM-5 crystalline zeolite comprise ZSM-11, ZSM-12, ZSM-35 and ZSM-38 crystalline zeolites.

EXAMPLE 1

The conversion of methanol to gasoline was evaluated in a two reactor sequentially arranged system using pure methanol as the feed. The catalyst used in the first reactor to dehydrate the methanol charge to dimethylether was a commercially available alumina calcined for 3 hours at 1000° F.

The reactor was operated adiabatically with an average temperature rise of 200° F at an inlet temperature of 470°–500° F. When syn-crude methanol (83 wt.% methanol - 17% water) was used as the feedstock to simulate commercial operation the alumina failed to maintain the adiabatic temperature rise at an inlet temperature of 500° F and methanol conversion dropped from the equilibrium value to no detectable conversion. An alumina dehydration catalyst that had been calcined at 1400° and 1700° F also failed to convert syn-crude methanol at reactor inlet temperatures of 450°–500° F. An in-situ recalcination of the deactivated alumina (calcined originally at 1000° F) at 950° F restored the activity but it rapidly decayed.

The concept of an in-situ restoration of the dehydration activity of deactivated alumina was first tested on an exploratory basis. The catalyst temperature profile was recorded at each of several inlet temperatures and the existence of a significant temperature rise (>10° F) in the catalyst bed was used as an index of activity. The catalyst used in these studies was commercially available alumina which had been calcined for three hours at 1300° F to give a large crystalline gamma alumina with a trace of delta alumina.

EXAMPLE 2

No temperature rise was observed in the catalyst bed when the reactor inlet temperature was 600° F or below and a nearly isothermal profile was obtained at 450°, 550° and 600° F. No conversion of methanol to dimethyl ether was detected and the catalyst was presumed to be deactivated due to surface rehydration at these temperatures. The reactor inlet temperature was increased from 600° to 700° and a 40° F temperature rise was observed at 700° F. This confirmed a hypothesis that the surface rehydration was a temperature reversible phenomena. Subsequent experiments were conducted to determine the reactor inlet temperature at which the surface rehydration occurred. The magnitude of the temperature rise decreased concomitantly as the reactor inlet temperature decreased, that is, 30° F at 675° F, 20° F at 650° F and 10° F at 625° F. When the inlet temperature was reduced to 600° F the isothermal profile was restored and methanol conversion was greatly diminished.

These observations led to the conclusion that the first stage dehydration catalyst be operated at a reactor inlet temperature of 600°–625° F. At this inlet temperature rehydration of the alumina should not occur and the alumina was expected to dehydrate the syn-crude methanol to equilibrium conversion levels. This concept was tested in a two-reactor, adiabatic pilot plant with an alumina calcined at 1400° F. The catalyst performed satisfactorily in that equilibrium conversion of methanol was achieved. A nearly adiabatic temperature profile was sustained throughout the run and the catalyst maintained its activity for more than 30 days on stream.

As above identified, in the processing combination of this invention, gamma alumina is used to convert methanol to dimethylether in a first reactor of a two reactor methanol to gasoline conversion process. It was found that changing the feed in such a system from 100% methanol to crude methanol comprising 17% water, greatly increased the first reactor catalyst aging rate and this increased aging rate was attributed to the hydration of the alumina catalyst employed. It was found upon careful investigation that the alumina is rapidly and reversibly deactivated by water at a reactor inlet temperature below 600° F. But when employing reactant inlet temperatures within the range of 625°–750° F, equilibrium conversion of the syn-crude methanol was maintained for a number of days on stream sufficient to imply little if any catalyst aging. It was further observed that methanol or dimethylether can be used as quench fluid to reduce a temperature rise in the methanol to gasoline catalyst system without experiencing undesirable effects in selectivity and uncontrolled durene production. This observation was reached by adding durene to the methanol feed to the process in amounts up to and exceeding that made in single pass processing of methanol alone. It was found that as the durene concentration is increased, a concentration is reached above which it is converted to other more desirable products; thus providing a steady state operation with respect to durene production. Furthermore it was observed that adding durene as above provided also increases the yield of aromatics at the higher temperature operating conditions. In addition these results indicate that the use of durene recycle will allow operation at conditions that are more favorable with respect to selectivity and catalyst aging without the consequence of high durene production.

The presence of durene (1,2,4,5 tetramethylbenzene) in high concentrations (>4 weight percent) in gasoline produced in the methanol conversion process is detrimental to engine performance since at those higher concentrations durene deposits on metal surfaces in, for example, the carburetor causing poor operation. The desirability of eliminating or severely restricting the presence of durene in a gasoline product is thus readily apparent.

DISCUSSION OF SPECIFIC EXAMPLES

A complete summary of the methanol-durene feedstock experiments is presented in Table 1 below. The yields of aromatics and durene as a function of normal catalyst temperature are presented in Table 2 below. The net production or depletion of durene across the catalyst sequence is presented in Table 3 in the form of a durene mass balance. The total aromatics, (BTX) benzene, toluene, xylene and $C_5$ plus yields versus average catalyst temperature are presented in FIGS. 1 through 3.

EXPERIMENTAL PROGRAM

A methanol feedstock which had been doped with durene to various concentration levels was passed over a methanol conversion catalyst comprising 35% alumina and 65% acid ZSM-5 ($SiO_2/Al_2O_3 = 70/1$) in the single pass mode of operation to determine whether the durene concentration in the reactor effluent approached a steady state or system equilibrium value.

The doped feedstocks were prepared by dissolving a sufficient amount of durene in pure methanol at room temperature to give 1 and 3 wt. % solution.

The single pass evaluations were carried out with the alumina dehydration catalyst in the first reactor and the zeolite conversion catalyst in the second reactor. The operating variables were the same for each feedstock studied, that is, the reactor outlet pressure was 150 psig, the nitrogen to methanol ratio was 2/1, the WHSV was 5.7 based on zeolite and the nominal, average catalyst temperatures were 750°, 800° and 850° F which cover a spectrum of temperatures that would be encountered.

from 760° to 860° F. The total aromatics and BTX yields decreased by 45% (33.8 to 18.4% wt. for aromatics and 13.2 to 7.4% wt. for BTX) when the temperature was increased. Durene yield was affected more severely by the increase in temperature, that is, it decreased by 70% wt. in going from greater than 6% wt. to less than 2% wt.

99% Methanol - 1% Durene

The presence of 1% wt. durene in the methanol feedstock showed no net increase in durene production at −800° and −850° F and in fact a substantial, 44%, decrease at −750° F. With respect to selectivity there was little or no decrease in total aromatics or BTX yield over the range of 750°–850° F while with the base case there was <40% reduction over the same temperature range. This indicates that the presence of durene in the feed has modified the aromatization activity of the catalyst. With respect to $C_5+$ yield the selectivity effect is similar to that observed for aromatics but to a somewhat lesser degree.

97% Methanol - 3% Durene

The presence of 3% wt. durene in the feed showed a net destruction of durene across the reactor system indicating that a system equilibrium with respect to durene concentration was obtained. The selectivity effects for total aromatics, BTX and $C_5+$ yields were similar to those observed for 1% durene in the feed.

Table 1

| Charge Stock | Summary of MeOH-Durene Feedstock Experiments | | | | | | | | | | | |
|---|---|---|---|---|---|---|---|---|---|---|---|---|
| | 100% MeOH | | | | 99% MeOH — 1% Durene | | | | 97% MeOH — 3% Durene | | | |
| Operating Conditions | | | | | | | | | | | | |
| Temp. (Avg.), °F | 762 | 811 | 812 | 861 | 763 | 804 | 803 | 854 | 763 | 764 | 813 | 860 |
| Temp. (Max.), °F | 818 | 836 | 842 | 883 | 803 | 821 | 816 | 875 | 799 | 799 | 838 | 881 |
| Pressure, psig | 150 | 150 | 150 | 150 | 150 | 150 | 150 | 150 | 150 | 150 | 150 | 150 |
| WHSV (Zeolite), h$^{-1}$ | 5.7 | 5.7 | 5.7 | 5.7 | 5.6 | 5.5 | 5.6 | 5.6 | 5.7 | 5.7 | 5.7 | 5.7 |
| Product Distribution, wt % | | | | | | | | | | | | |
| Hydrocarbon | 43.3 | 41.5 | 51.6 | 43.0 | 40.9 | 43.5 | 41.9 | 43.3 | 41.7 | 43.5 | 43.6 | 44.1 |
| Water | 56.1 | 57.7 | 57.5 | 51.3 | 58.3 | 55.6 | 57.1 | 55.8 | 58.0 | 56.1 | 55.3 | 55.5 |
| CO | 0.4 | 0.6 | 0.7 | 1.1 | 0.7 | 0.9 | 0.8 | 0.9 | 0.4 | 0.3 | 0.4 | 0.4 |
| HC Analysis, wt % | | | | | | | | | | | | |
| $C_5+$ Yield | 59.4 | 55 | 55 | 48.3 | 57.6 | 53.1 | 57.1 | 53.4 | 52.9 | 57.3 | 55.1 | 51.2 |
| Aromatics Total | 33.8 | 23.4 | 21.6 | 18.4 | 26.4 | 24.9 | 25.5 | 25.6 | 25.8 | 25.2 | 24.1 | 24.4 |
| BTX | 13.2 | 9.0 | 7.8 | 7.4 | 8.9 | 7.2 | 8.0 | 9.6 | 7.5 | 6.5 | 7.1 | 8.1 |
| Durene | 6.3 | 3.4 | 3.3 | 1.9 | 6.5 | 5.2 | 5.6 | 4.0 | 6.6 | 6.7 | 5.2 | 4.2 |
| Olefins Total | 3.5 | 10.7 | 14.6 | 21.4 | 5.7 | 15.8 | 13.7 | 22 | 3.8 | 5.7 | 10.5 | 16.6 |

100% Methanol - 0% Durene

A pure methanol experiment was conducted to provide a base case for comparison of catalyst performance with the durene doped feedstocks. The $C_5+$ yield decreased from the 60% wt. level to less than 50% when the average catalyst temperature was increased Table 2

| Nominal Catalyst Temperature, °F | Aromatics-Durene Yields as a Function of Catalyst Temperature | | | | | | | | |
|---|---|---|---|---|---|---|---|---|---|
| | 750 | | | 800 | | | 850 | | |
| Operating Conditions | | | | | | | | | |
| Feed Stock, wt % | | | | | | | | | |
| MeOH | 100 | 99 | 97 | 100 | 99 | 97 | 100 | 99 | 97 |
| Durene | 0 | 1 | 3 | 0 | 1 | 3 | 0 | 1 | 3 |
| Temp., (Avg.), °F | 762 | 763 | 764 | 812 | 804 | 813 | 861 | 854 | 860 |
| Temp., (Max.), °F | 818 | 803 | 799 | 836 | 818 | 838 | 883 | 875 | 881 |
| Pressure, psig | 150 | 150 | 150 | 150 | 150 | 150 | 150 | 150 | 150 |
| WHSV (Zeolite), h$^{-1}$ | 5.7 | 5.6 | 5.7 | 5.7 | 5.6 | 5.7 | 5.7 | 5.6 | 5.6 |
| Product Distr'n | | | | | | | | | |
| HC Analysis, wt % | | | | | | | | | |
| $C_5+$ Yield | 59.4 | 57.6 | 55.1 | 55 | 55.1 | 55.1 | 48.3 | 53.4 | 51.2 |
| Aromatics Total | 33.8 | 26.4 | 25.5 | 22.5 | 25.2 | 24.1 | 18.4 | 25.6 | 24.4 |
| Durene | 6.3 | 6.5 | 6.7 | 3.4 | 5.4 | 5.2 | 1.9 | 4.0 | 4.2 |

Table 3

| Production/Consumption of Durene[b] in Feedstock Doping Experiments | | | |
|---|---|---|---|
| Average Catalyst Temperature (F) | Durene Content Feedstock (g) | Durene Content Hydrocarbon Product (g) | Net Change[a] Across Reactor (g) |
| 762 | 0 | 8.2 | +8.2 |
| 812 | 0 | 4.0 | +4.0 |
| 861 | 0 | 2.3 | +2.3 |
| 763 | 2.8 | 7.4 | +4.6 |
| 804 | 2.8 | 6.8 | +4.0 |
| 854 | 2.8 | 5.1 | +2.3 |
| 764 | 8.4 | 7.8 | −0.6 |
| 813 | 8.4 | 6.1 | −2.3 |
| 860 | 8.4 | 5.3 | −3.1 |

[a](+) net production of durene  (−) net consumtion of durene
[b]Based on six-hour material balance.

The concept of a multiple catalyst bed methanol conversion arrangement with interbed injection of methanol or dimethylether as a quench stream has been heretofore approached with caution for fear that this mode of operation would lead to excessive durene concentrations in the hydrocarbon product. It was proposed that the overall reaction leading to the formation of durene could be written

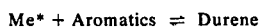

Me* + Aromatics ⇌ Durene where Me* represents a reactive intermediate (either a hydrocarbon fragment or an oxygenate) formed from methanol or dimethylether. Thus it was proposed that the injection of methanol into the effluent stream from the nth catalyst bed would cause a shift to higher durene concentrations in the upper region of the n+1 bed due to the favorable conditions for durene formation, that is, high methanol concentration, lower catalyst temperature (<750° F) and the presence of aromatics. Furthermore, it was presumed a similar increase in durene concentration would occur in each bed such that the concentration of durene in the effluent from the final bed would render the gasoline product unacceptable without further processing to reduce the durene content.

Contrary to these speculations, the experiments carried out in this investigation indicate that durene does not accumulate but is converted, that is, the durene in excess of the apparent equilibrium concentration is converted via isomerization, transalkylation and/or dealkylation to other aromatic species.

The presence of durene in the feedstock modified the aromatization function of the catalyst (FIGS. 1 and 2) in that at low temperature (~750° F) the aromatization activity was suppressed and at high temperature (~850° F) it was enhanced.

Referring now to FIG. 1 it will be observed that the downwardly sloping curve for the 100% methanol charge free of durene, is a high aromatic producer at temperatures within the range of 750° F to about 800° F as compared with the curves for the methanol charges comprising 1 and 3 percent durene.

FIG. 2 on the other hand directed to identifying yields of benzene, toluene and xylene shows that for the pure methanol feed at temperatures within the range of 750° to about 810° F the yields of BTX are higher than obtained with the durene doped methanol feed.

FIG. 4 is a diagrammatic sketch in elevation of a process arrangement for practicing the concepts of the present invention directed to the conversion of methanol to gasoline boiling range materials.

Figure 1:
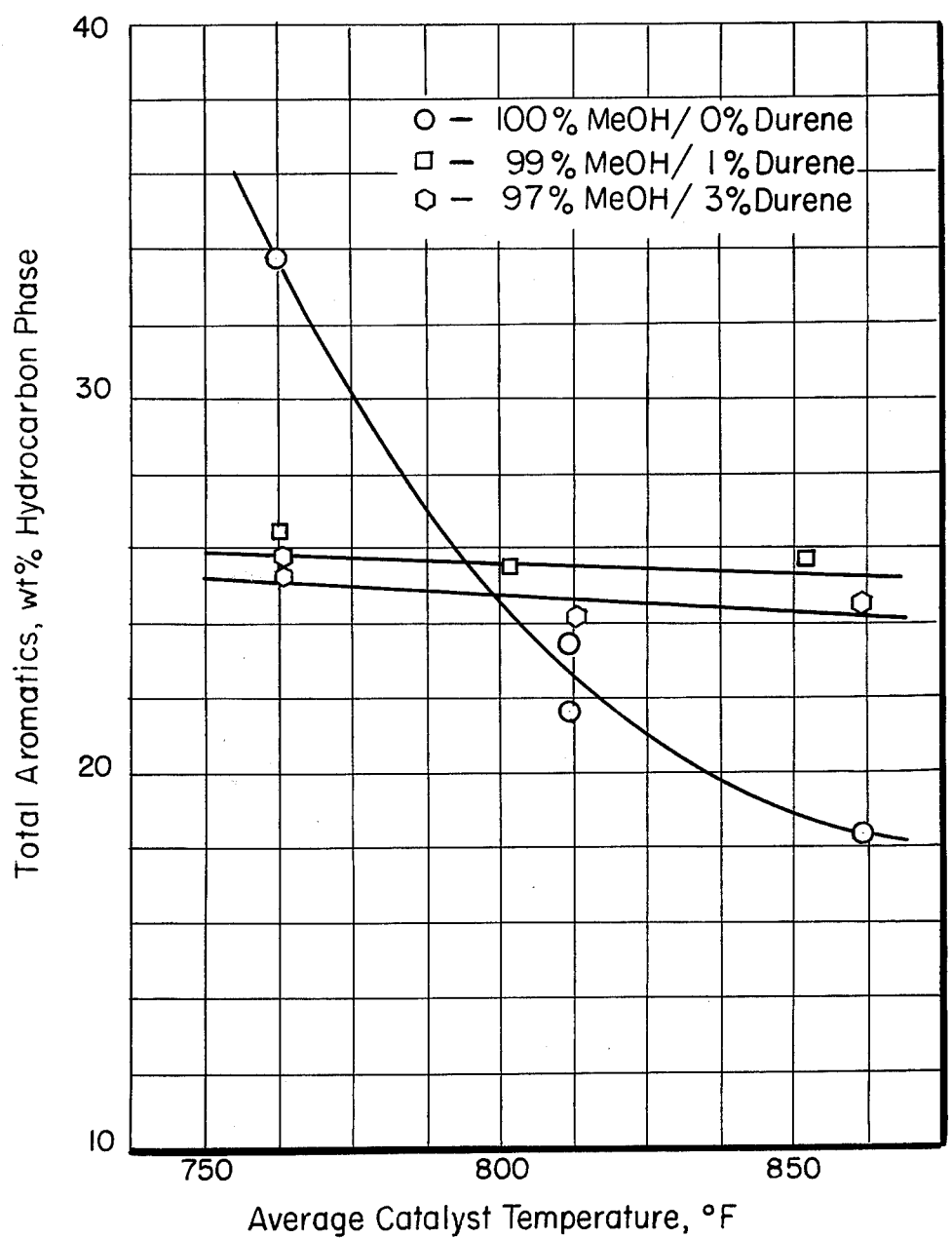

Referring now to the drawing, a methanol rich feed with or without combined water is charged to the process by conduit 2. The methanol feed preheated to a temperature equal to or greater than about 650° F by means not shown is passed to the first of a series of catalyst contact zones maintained in reactor 4 as a bed of catalyst 6. Catalyst bed 6 comprises a calcined alumina above discussed which is used for affecting dehydration of the methanol charge to particularly produce a dimethylether product, unconverted methanol and water. The dehydration zone comprising catalyst bed 6 is maintained at a pressure within the range of 50 to 500 psig. In order to reduce the pressure drop in reactor 4, the fixed catalyst bed may be arranged for radial flow of reactant material through the catalyst mass by an axially positioned product withdrawal conduit. It is also contemplated employing a fixed fluid bed of the dehydration catalyst in reactor 4.

The product of methanol dehydration, water and uncombined methanol is passed from reactor 4 by conduit 8 to a separation zone 10 after cooling thereof by means not shown in conduit 8. The separation zone 10 may be either a simple condenser or a fractionation tower depending upon the degree of purity of DME desired. Operation of the separation zone would be at a pressure intermediate between that of the dehydration zone and the zeolite catalyst conversion zone at a temperature commensurate with the degree of separation desired. The water methanol mixture is passed to a separation zone 16 wherein a separation is made to recover a methanol rich stream from a water stream. The water stream is withdrawn by conduit 20. The methanol rich stream is recovered and passed by conduit 18 to conduit 2 for recycle to the dehydration zone. On the other hand all or a portion of this cool methanol recycle stream may be withdrawn by conduit 21 and used as quench fluid as more fully discussed below.

The dimethylether product of the alumina dehydration catalyst herein discussed is recovered by conduit 12 and passed to the second of a series of catalyst contact zones retained in reactor 22. The catalyst is distributed in a plurality of separate catalyst beds 24 in reactor 22 and comprises a crystalline zeolite of the special class of crystalline zeolites herein defined. In a specific arrangement the crystalline zeolite conversion catalyst comprises ZSM-5 which catalyst is arranged in a plurality of sequential catalyst beds for flow of reactants therethrough. The catalyst beds are separated from one another to provide space for contacting quench fluid material with product separated from each bed of catalyst. Furthermore each catalyst bed is arranged in thickness to restrict the ΔT exothermic temperature rise in each bed not to exceed about 50° per bed and not to exceed more than about 200° between the reactor 22 inlet and reactor product 34 outlet temperatures. The catalyst beds thus may increase in thickness in the direction of reactant flow therethrough.

To facilitate maintaining the temperature control above recited, it is proposed to introduce a quench fluid between the beds of catalyst. Thus a portion of the dimethylether charge may be passed by distributor manifold or conduit 26 to distributor conduits 28 communicating therefrom with the space in the reactor between beds of catalyst. On the other hand recycle methanol withdrawn by conduit 21 may be charged to distributor conduit 26 by conduit 30. Conduit 30 may also be employed to introduce light hydrocarbons as quench fluid as discussed above. On the other hand recycle $C_{10}$ aromatic product hydrocarbons and particularly the durene portion thereof may be recycled and introduced as quench fluid with any one of the quench fluids or a combination thereof above defined.

The zeolite catalyst conversion zone 22 is charged with the dimethylether (DME) feed suitably preheated as by heat exchanger 32 to provide an inlet temperature of at least about 550° F. As mentioned above, the zeolite catalyst exothermic conversion operation is preferably within the temperature range of 600° to 850° F. and within the pressure range of 50-500 psig.

A gasoline boiling range product comprising $C_5$ and higher boiling material is recovered from the reactor 22 by conduit 34 and passed to a separation zone 36. In separation zone 36 temperature and pressure conditions are selected to permit the recovery of $C_9$ and lower boiling material withdrawn by conduit 35 from $C_{10}$ and higher boiling material. The $C_{10}$ plus product material is passed by conduit 40 from separator 36 to a separation zone 42. Separation zone 42 is preferably a crystallization zone wherein a separation is made between $C_{10}$ materials by such a technique. For example durene forms crystals at a much higher temperature 79°-80° C than isodurene 24° C and other derivatives thereof and can be separated by filter means not shown or by other suitable means. In this operation the durene is recovered and recycled by conduit 44 to the zeolite catalyst conversion operation. The remaining $C_{10}$ materials are recovered from zone 42 by conduit 46. Isodurene is a high octane product and may be combined with the gasoline product of the process such as recovered by conduit 38. It is also contemplated by passing the crystallization step in zone 42 and recycling all of the $C_{10}$ material in conduit 40 by conduit 44 to reactor 22.

Having thus generally discussed the concepts of the invention and specifically discussed examples in support thereof, it is to be understood that no undue restrictions are to be imposed by means thereof except as defined by the following claims.

We claim:

1. In a method for converting methanol to gasoline boiling products in a plurality of sequentially arranged catalyst beds which comprises, effecting a catalytic restructuring of the methanol feed to an ether rich product in at least one catalyst contact zone under selected temperature conditions, effecting a catalytic restructuring of the ether rich product to form aromatics and isoparaffins boiling in the gasoline boiling range in at least one other catalyst contact zone employing a crystalline zeolite of the class represented by ZSM-5 crystalline zeolite, the improvement comprising effecting control of the exothermic temperature rise in any one bed of crystalline zeolite catalyst not to exceed about 50° F. by employing with the ether rich feed one or a combination of heat dissipating materials selected from the group consisting of $C_5$ and lower boiling hydrocarbons, a cooled methanol stream alone or in combination with a water free cool ether product fraction or a cool durene rich product fraction of the process.

2. The method of claim 1 wherein the methanol feed is converted to an ether rich product over an alumina catalyst at an initial inlet temperature of at least 600° F.

3. The method of claim 2 wherein the alumina catalyst is calcined at a temperature of 1400° F. for three hours.

4. The method of claim 1 wherein conversion of the methanol feed to an ether rich product is accomplished with an alumina catalyst at a temperature within the range of 625° to 750° F.

5. The method of claim 1 wherein a durene rich product is recovered and charged with the methanol feed to increase the yield of aromatics during high temperature operating conditions.

6. The method of claim 1 wherein a pure methanol feed substantially free of water may be charged at a lower temperature than a methanol feed containing substantial amounts of water.

7. The method of claim 1 wherein water and unconverted methanol are separated from the ether product before the ether product contacts the crystalline zeolite catalyst.

8. The method of claim 1 wherein up to 3 weight percent of durene based on feed is combined with the methanol feed and converted to desired products at a temperature within the range of 750° F. to 850° F.

Figure 2:
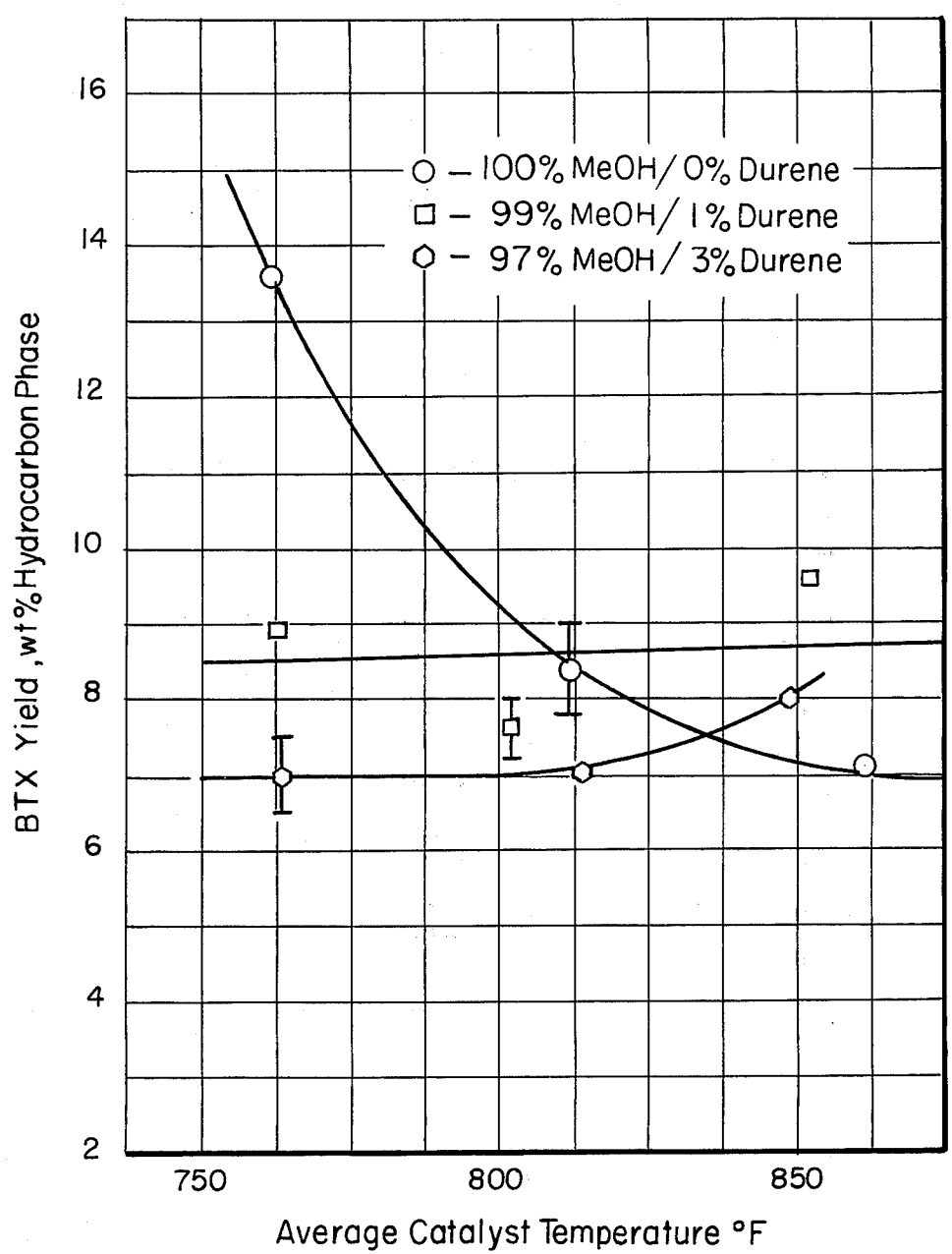

9. The method of claim 1 wherein the yield of total aromatics and BTX rich material are selected as a function of temperature and weight percent of durene in the methanol feed as represented by the graphs of FIGS. 1 and 2 respectively.

Figure 3:
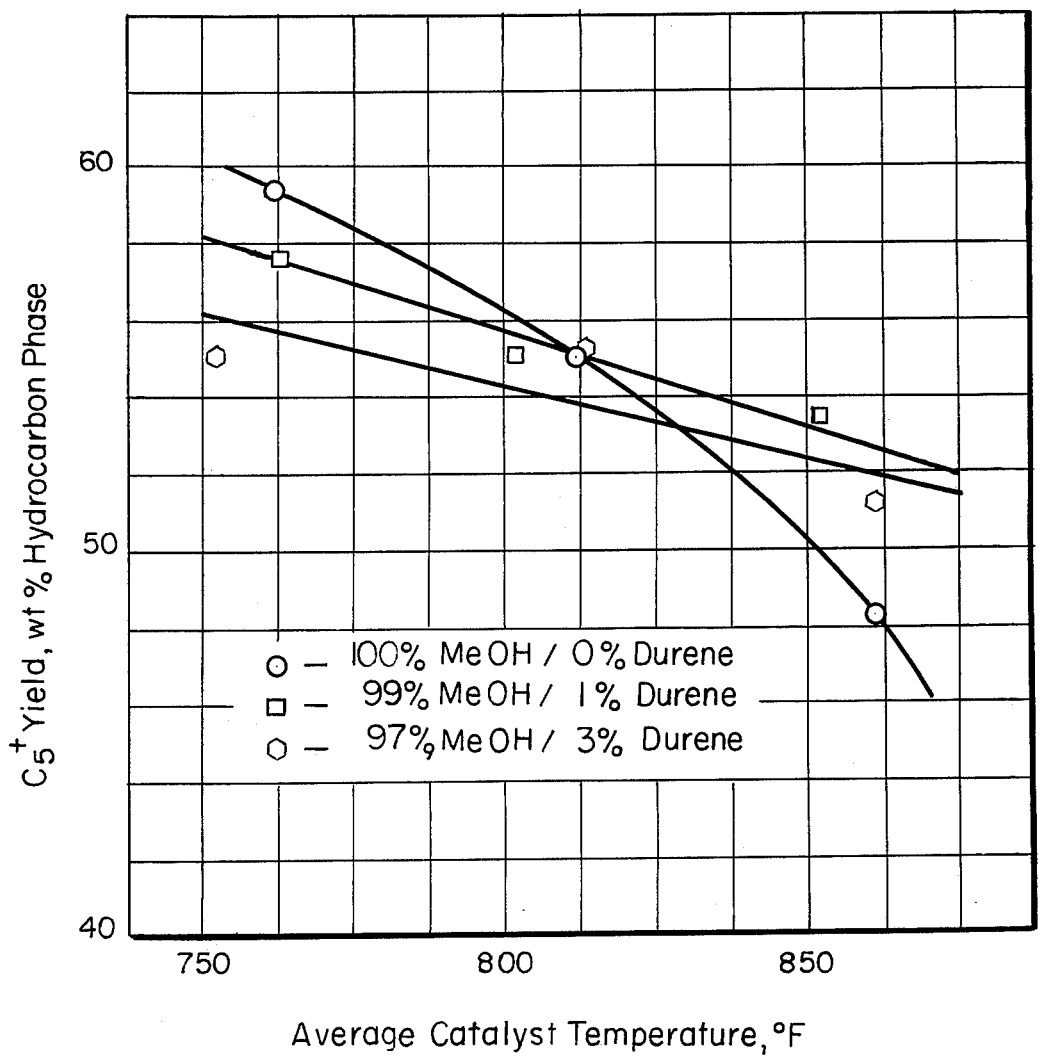
FIG. 3 shows a similar relationship in the $C_5$ plus yield. More significantly however the figures show that at temperatures above about 800° F, the durene doped methanol produces higher yields of desired products.

10. The method of claim 1 wherein the yield of $C_5$ plus product is selected as a function of temperature and weight percent of durene in the methanol feed as represented by the graph of FIG. 3.

11. The method of claim 1 wherein the crystalline zeolite catalyst is arranged in a plurality of separate catalyst beds of increasing thickness in the direction of reactant flow and the heat dissipating material is added between catalyst beds to restrict the exothermic temperature rise over the plurality of catalyst beds not to exceed about 200° F.

* * * * *